US009868482B2

(12) United States Patent
Rust et al.

(10) Patent No.: US 9,868,482 B2
(45) Date of Patent: Jan. 16, 2018

(54) TRACK ROLLER ASSEMBLY WITH A WEAR MEASUREMENT SYSTEM

(71) Applicant: CATERPILLAR INC., Peoria, IL (US)

(72) Inventors: Craig Richard Rust, Edwards, IL (US); Mark Steven Diekevers, Germantown Hills, IL (US)

(73) Assignee: Caterpillar Inc., Peoria, IL (US)

( * ) Notice: Subject to any disclaimer, the term of this patent is extended or adjusted under 35 U.S.C. 154(b) by 271 days.

(21) Appl. No.: 14/527,625

(22) Filed: Oct. 29, 2014

(65) Prior Publication Data

US 2016/0121945 A1 May 5, 2016

(51) Int. Cl.
*B62D 55/14* (2006.01)
*B62D 55/15* (2006.01)
*B62D 55/08* (2006.01)
*G01N 3/56* (2006.01)

(52) U.S. Cl.
CPC ............. *B62D 55/14* (2013.01); *B62D 55/08* (2013.01); *B62D 55/15* (2013.01); *G01N 3/56* (2013.01)

(58) Field of Classification Search
None
See application file for complete search history.

(56) References Cited

U.S. PATENT DOCUMENTS

| | | |
|---|---|---|
| 3,815,426 A | 6/1974 | Rohner |
| 3,958,445 A | 5/1976 | Howard |
| 4,689,557 A * | 8/1987 | Smith ................ G01P 3/488 324/174 |
| 4,790,190 A | 12/1988 | Bambara et al. |
| 4,928,521 A | 5/1990 | Jardine |
| 5,025,595 A * | 6/1991 | Orain ................ B24B 11/00 451/28 |
| 5,031,303 A * | 7/1991 | Orain ................ B23Q 3/062 269/156 |
| 5,085,519 A * | 2/1992 | Dougherty ........... F16C 19/386 324/173 |
| 5,348,515 A | 9/1994 | Miller |
| 5,436,612 A | 7/1995 | Aduddell |
| 5,636,026 A | 6/1997 | Mian et al. |

(Continued)

FOREIGN PATENT DOCUMENTS

| | | |
|---|---|---|
| EP | 2175423 A2 | 4/2010 |
| EP | 2548665 A1 | 1/2013 |

(Continued)

OTHER PUBLICATIONS

Zhange, Z X et al., Measurements of cutter forces and cutter temperature of boring machine in Aspo Hard Rock Laboratory, Tech. Rpt TR-01-34, Apr. 2001, Stockholm, Sweden.

(Continued)

*Primary Examiner* — Shelley Chen

(57) ABSTRACT

A roller of an undercarriage track system for a machine is disclosed. The roller includes a body and a sensed feature. The body is a solid of revolution formed about a roller axis. The body includes a bore surface and a roller contact surface. The bore surface defines a bore extending through the body. The bore surface is a radially inner surface of the body. The roller contact surface is located outward from the bore surface. The sensed feature is located at the body. The sensed feature is configured to rotate with the body and to be detectable by a sensor.

8 Claims, 3 Drawing Sheets

(56) References Cited

U.S. PATENT DOCUMENTS

| | | | |
|---|---|---|---|
| 5,954,186 A * | 9/1999 | Stroobandt | B65G 43/04 198/502.4 |
| 6,024,183 A | 2/2000 | Dietz et al. | |
| 6,027,185 A | 2/2000 | Crabb | |
| 6,107,917 A | 8/2000 | Carrender et al. | |
| 6,250,429 B1 | 6/2001 | Kramer | |
| 6,276,768 B1 | 8/2001 | Miller | |
| 6,305,763 B1 | 10/2001 | Oertley | |
| 6,354,678 B1 | 3/2002 | Oertley | |
| 6,360,850 B1 | 3/2002 | Odisho et al. | |
| 6,431,008 B1 | 8/2002 | Oertley et al. | |
| 6,477,893 B1 | 11/2002 | Djordjevic | |
| 6,569,046 B1 | 5/2003 | Gregg | |
| 6,682,155 B2 | 1/2004 | Hoff et al. | |
| 6,845,306 B2 | 1/2005 | Henry et al. | |
| 6,868,711 B2 | 3/2005 | Ebi | |
| 6,948,783 B2 | 9/2005 | Hoff | |
| 7,014,271 B2 | 3/2006 | Burger et al. | |
| 7,032,740 B2 | 4/2006 | Hochhaus et al. | |
| 7,172,257 B2 | 2/2007 | Tamaru et al. | |
| 7,177,553 B2 | 2/2007 | Ono | |
| 7,210,750 B2 | 5/2007 | Yamamoto et al. | |
| 7,237,631 B2 | 7/2007 | Livesay | |
| 7,239,242 B2 | 7/2007 | Ghosh | |
| 7,374,257 B2 | 5/2008 | Oertley | |
| 7,507,965 B2 | 3/2009 | Lane et al. | |
| 7,540,374 B2 | 6/2009 | Rathbun et al. | |
| 7,698,946 B2 | 4/2010 | Clarke et al. | |
| 7,764,173 B2 | 7/2010 | Yamagiwa | |
| 7,908,928 B2 | 3/2011 | Vik et al. | |
| 7,914,086 B2 | 3/2011 | Mulligan | |
| 8,100,483 B2 | 1/2012 | Diekevers et al. | |
| 8,169,311 B1 | 5/2012 | Breed | |
| 8,326,549 B2 | 12/2012 | Ishizaki et al. | |
| 8,335,606 B2 | 12/2012 | Mian et al. | |
| 8,398,182 B2 | 3/2013 | Simula et al. | |
| 8,426,813 B2 | 4/2013 | Furry | |
| 8,540,325 B2 | 9/2013 | Diekevers et al. | |
| 8,543,283 B2 | 9/2013 | Boss et al. | |
| 8,596,126 B2 | 12/2013 | Oliver et al. | |
| 8,600,611 B2 | 12/2013 | Seize | |
| 9,347,763 B2 * | 5/2016 | Ikegami | E02F 9/2271 |
| 2002/0116992 A1 | 8/2002 | Rickel | |
| 2006/0044146 A1 | 3/2006 | Ferguson et al. | |
| 2006/0243839 A9 | 11/2006 | Barscevicius et al. | |
| 2007/0044447 A1 | 3/2007 | Viaud | |
| 2007/0088523 A1 | 4/2007 | Keller et al. | |
| 2009/0099886 A1 | 4/2009 | Greiner et al. | |
| 2009/0297273 A1 | 12/2009 | Lindbergh et al. | |
| 2009/0313860 A1 | 12/2009 | Breiner et al. | |
| 2010/0013594 A1 | 1/2010 | Komine et al. | |
| 2011/0046857 A1 | 2/2011 | Farmer et al. | |
| 2012/0043980 A1 | 2/2012 | Davies | |
| 2013/0082846 A1 | 4/2013 | McKinley et al. | |
| 2013/0186732 A1 * | 7/2013 | Bugar | B65G 23/00 198/502.1 |
| 2013/0255354 A1 * | 10/2013 | Hawkins | G01N 3/56 73/7 |
| 2014/0105481 A1 | 4/2014 | Hasselbusch et al. | |
| 2014/0125117 A1 | 5/2014 | Weeks et al. | |
| 2014/0229120 A1 | 8/2014 | Luharuka et al. | |
| 2014/0311762 A1 | 10/2014 | Behmlander et al. | |
| 2015/0267382 A1 * | 9/2015 | Ikegami | E02F 3/435 92/5 R |

FOREIGN PATENT DOCUMENTS

| | | |
|---|---|---|
| JP | 2000042894 A | 2/2000 |
| KR | 101087961 B1 | 12/2011 |
| WO | 99/51996 | 10/1999 |
| WO | 2006/116758 A2 | 11/2006 |
| WO | 2010/117331 A1 | 10/2010 |
| WO | 2013/057275 A1 | 4/2013 |
| WO | 2014/000507 A1 | 1/2014 |

OTHER PUBLICATIONS

Shanahan, Aaron, "Cutter Instrumentation System for Tunnel Boring Machines", pp. 110-115, The Robbins Company, Kent, Washington.

De Broissia, M. et al., "Global Optimisation of Disc Cutter Tool Life for Tunnel Boring Machine Preparing 4th Eurothen Workshop" Bougues Travaux Publics., Mar. 1, 2000, Guyancourt, France.

EPO International Search Report, PCT/US2006/016518, dated Nov. 8, 2006.

EPO International Search Report, PCT/US2012/057831, dated Dec. 18, 2012.

EPO International Search Report, PCT/US2015/057474, dated Jan. 14, 2016.

* cited by examiner

TRACK ROLLER ASSEMBLY WITH A WEAR MEASUREMENT SYSTEM

TECHNICAL FIELD

The present disclosure generally pertains to undercarriage track systems, and is directed toward a track roller assembly with a wear measurement system for mining and construction machinery.

BACKGROUND

Mining and construction machines, such as hydraulic mining shovels, excavators, wheel loaders, cable shovels, bucket wheels, and draglines commonly employ undercarriage track systems. The undercarriage track systems generally employ a track chain assembly formed by interconnected track links. The track chain assembly is generally guided and supported by rollers. The contact between the track links and the rollers may create high stresses, which can cause, inter alia, wear along contact surfaces of the rollers and track links.

The undercarriage track system may be monitored to determine when to service the undercarriage track system. U.S. Patent application No. 2013/0255354 to Hawkins et al., for example, discloses an undercarriage monitoring device having a roller assembly including a fixed roller component and a bushing. An opening is formed within the fixed roller component. A first sensor is disposed within the opening of the fixed roller component over the bushing. The first sensor is configured to sense a first physical characteristic of the bushing. The fixed roller component is a shaft or a housing. The first sensor is a temperature sensor or a Hall effect sensor. A magnet is disposed on the roller assembly. A second sensor is disposed within the opening of the fixed roller component over the bushing. The second sensor is configured to sense a second physical characteristic of the bushing. A data transmitting device is coupled to the first sensor. Data is collected from the sensor. The data collected from the sensor is transmitted to a receiving device.

The present disclosure is directed toward overcoming one or more of the problems discovered by the inventors.

SUMMARY OF THE DISCLOSURE

A roller of an undercarriage track system for a machine is disclosed. In embodiments, the roller includes a body and a sensed feature. The body is a solid of revolution formed about a roller axis. The body includes a bore surface and a roller contact surface. The bore surface defines a bore extending through the body. The bore surface is a radially inner surface of the body. The roller contact surface is located outward from the bore surface. The sensed feature is located at the body. The sensed feature is configured to rotate with the body and to be detectable by a sensor.

DETAILED DESCRIPTION

The systems and methods disclosed herein include a roller of an undercarriage track system for a machine. In embodiments, the roller includes a sensed feature that is detectable by a sensor. The sensor is configured to detect the sensed feature to track the revolutions of the roller. The revolutions tracked by the sensor may be used to determine a rotational speed of the roller, which can be compared to the translational speed of the machine to determine wear on the roller. Determining the wear on the roller may allow an operator or an original equipment manufacturer to predict further wear on the roller and to determine when to schedule maintenance on the machine.

Figure 1:
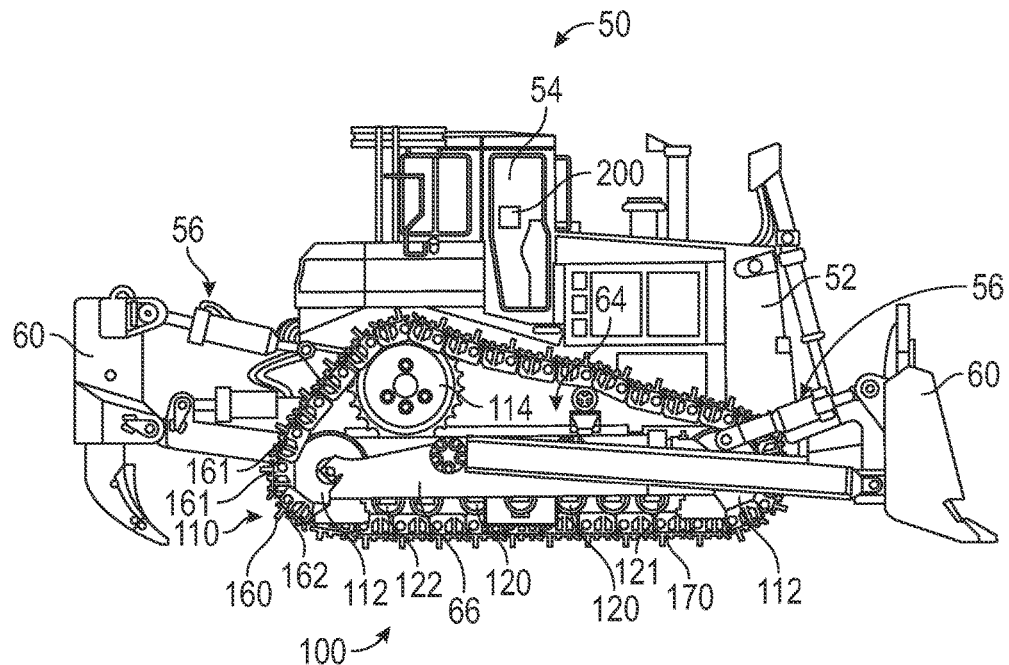
FIG. 1 is a diagrammatic side elevational view of an embodiment of a machine including an undercarriage track system.

FIG. 1 is a diagrammatic side elevational view of an embodiment of a machine 50 including an undercarriage track system 100. The term "machine" may refer to any machine that that performs some type of operation associated with an industry such as mining or construction, or any other industry known in the art, such as a hydraulic mining shovel, an excavator, a track-type tractor (bulldozer), a wheel loader, a cable shovel, a dragline, or the like. In the embodiment illustrated, the machine 50 is a track-type tractor.

The machine 50 may include a machine body 52, one or more hydraulic systems 56, one or more ground engaging implements 60, and an undercarriage structure 64. The machine body 52 may include a cab 54 to house a machine operator. An electronic control system 200 can be housed in the cab 54 that can be adapted to allow a machine operator to manipulate and articulate the ground engaging implements 60 for any suitable application.

A hydraulic system 56 may connect at one end to the machine body 52 and may support a ground engaging implement 60 at an opposing, distal end. In embodiments, the ground engaging implement 60 can be any suitable implement, such as a bucket, a clamshell, a blade, a shank, or any other type of suitable device. In the embodiment illustrated, a ground engaging implement is connected to each end of the machine body 52.

The undercarriage structure 64 may include a supporting structure 66 and an undercarriage track system 100. The supporting structure 66 may connect the undercarriage track system 100 to the machine body 52 and may support the undercarriage track system 100.

The undercarriage track system 100 may include a track roller frame assembly 110 and an associated track chain assembly 160 on each side of the undercarriage structure 64. It will be appreciated that only one track roller frame assembly 110 and only one track chain assembly 160 is visible in FIG. 1.

Figure 2:
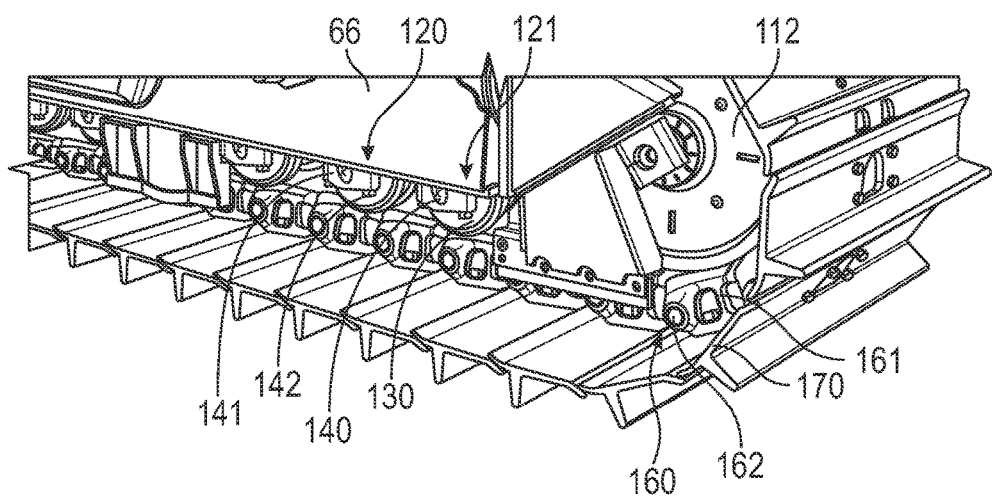
FIG. 2 is a perspective view of a portion of the undercarriage track system.

FIG. 2 is a perspective view of a portion of the undercarriage track system 100. Referring to FIGS. 1 and 2, each track roller frame assembly 110 may include one or more idler wheels 112, a drive sprocket wheel 114, and track roller assemblies 120. In the embodiment illustrated, an idler wheel 112 is coupled to each end of the supporting structure 66. The drive sprocket wheel 114 may also be coupled to the supporting structure 66. In the embodiment illustrated, the drive sprocket wheel 114 is adjacent the idler wheel 112 coupled to the aft end of the supporting structure 66. In other embodiments, with one idler wheel 112, the drive sprocket wheel 114 may be positioned at the end of the supporting structure 66 opposite the idler wheel 112. The drive sprocket wheel 114 is powered in forward and reverse directions by an engine of machine 50. The drive sprocket wheel 114 drives the track chain assembly 160 to move the machine 50.

Track roller assemblies 120 may be positioned between the ends of the supporting structure 66 and at least partially below the supporting structure 66. In the embodiment illustrated, the roller assemblies 120 are positioned between the two idler wheels 112. In other embodiments, the roller assemblies 120 are positioned between an idler wheel 122 and the drive sprocket wheel 114. The roller assemblies 120 may include a front roller assembly 121 may be positioned adjacent the idler wheel 112 at the front end of the supporting structure 66 and a rear roller assembly 122 may be positioned adjacent the idler wheel 112 at the rear end of the supporting structure 66. Idler wheels 112 and track roller assemblies 120 may be configured to guide a track chain assembly 160 around the supporting structure 66.

In embodiments, each track chain assembly 160 includes track links 161 inter-connected and linked together by track pins 162 to form a closed chain. In the embodiment illustrated, track links 161 are connected to, such as by fastening, ground engaging shoes 170. The ground engaging shoes 170 or ground engaging portions may be configured to overlap. In other embodiments, each track chain assembly 160 includes track pads inter-connected and linked together. The track pads may include a track link and a ground engaging shoe that are cast or forged as an integral unit.

Referring to FIG. 2, each track roller assembly 120 may include a roller 130, a roller shaft 140, a sensor 150 (shown in FIG. 3), roller bearing assemblies 149 (shown in FIGS. 3 and 4), roller connection hardware 141, and roller connectors 142 configured to couple the roller connection hardware 141 to supporting structure 66. Roller connection hardware 141 may be located adjacent each end of roller 130 and may be configured to support each end of roller shaft 140. Roller connection hardware 141 may prevent roller shaft 140 from rotating.

Figure 3:
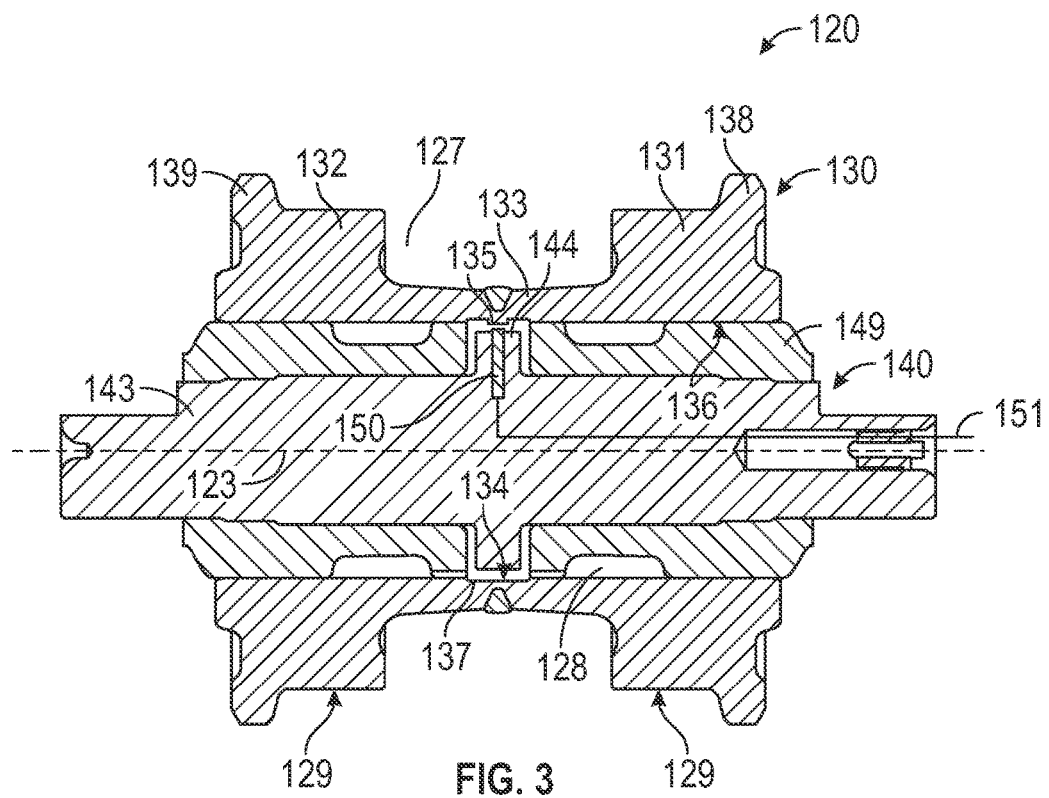
FIG. 3 is a cross-sectional view of an embodiment of a track roller assembly of FIGS. 1 and 2.

FIG. 3 is a cross-sectional view of an embodiment of a portion of a track roller assembly 120 of FIGS. 1 and 2. Roller 130 may generally be a solid of revolution formed by revolving a closed shape about a roller axis 123 with the closed shape offset from the roller axis 123 forming a bore 128 extending there through. Roller 130 may include one or more roller contact surfaces 129. Each roller contact surface 129 may be a surface of revolution revolved about roller axis 123. In the embodiment illustrated, roller 130 includes two roller contact surfaces 129 spaced apart with each roller contact surface 129 being a right circular cylinder. In some embodiments, roller 130 includes a single roller contact surface 129 with a concave shape, such as a catenoid or a hyperboloid, extending between each side of the roller 130.

In the embodiment illustrated, roller 130 includes a body 133, a first guide 138, a second guide 139, and a sensed feature 135. Body 133 may be a solid of revolution with the bore 128 extending there through. Bore 128 may generally be defined by a bore surface 136. Bore surface 136 defines the inner surface of body 133 and may generally be a cylindrical shape, such as a right circular cylinder. Bore 128 is configured to receive roller shaft 140 and roller bearing assemblies 149. In some embodiments, bore 128 includes an inner recess 137 extending into body 133 from bore surface 136. Inner recess 137 may include an annular shape. Inner recess 137 may include a recess surface 134.

Body 133 may include a first roller contact flange 131 and a second roller contact flange 132. First roller contact flange 131 extends at one end of body 133. First roller contact flange 131 includes a roller contact surface 129. The roller contact surface 129 may be the outer surface of body 133 and of first roller contact flange 131. Second roller contact flange 132 extends at the other end of body 133 opposite first roller contact flange 131. Second roller contact flange 132 is spaced apart from first roller contact flange 131 forming an outer recess 127 there between. Second roller contact flange 132 also includes a roller contact surface 129. The roller contact surface 129 may be the outer surface of second roller contact flange 132. The first roller contact flange 131 and the second roller contact flange 132 may be configured to contact track links 161 or a portion of track links 161.

First guide 138 may extend outward from an end of first roller contact flange 131 distal to second roller contact flange 132. Second guide 139 may extend outward from an end of second roller contact flange 132 distal to first roller contact flange 131. First guide 138 and second guide 139 may be configured to maintain the alignment of the track links 161 relative to the rollers 130.

Sensed feature 135 is a feature configured to be detected by a sensor 150. Sensed feature 135 is located at body 133, such as on or in body 133. Sensed feature 135 may be a protrusion, such as a tooth, or a recess, such as a slot. Sensed feature 135 may protrude from or into body 133. In the embodiment illustrated in FIG. 3, sensed feature 135 is a tooth extending inward from body 133 and into bore 128. In embodiments, sensed feature 135 is a slot that is an inverse of the tooth shape illustrated in FIG. 3. Sensed feature 135 may be located at or near the middle of bore 128. Sensed feature 135 may be integral to body 133, may be metallurgically joined to body 133, such as by brazing or welding, or may be a pressed-in piece. In the embodiment illustrated, roller 130 includes a single sensed feature 135 extending inward from recess surface 134. In other embodiments, roller 130 includes more than one sensed feature 135.

Roller shaft 140 extends through roller 130 at bore 128. Roller shaft 140 may include a shaft body 143 and a shaft flange 144. Shaft body 143 may generally include a right circular cylinder shape. Shaft flange 144 may extend outward from shaft body 143. Shaft flange 144 may be integral to shaft body 143. Shaft flange 144 may include a diameter slightly smaller than the diameter of bore 128.

Roller bearing assemblies 149 may be located between roller 130 and roller shaft 140 in bore 128. In the embodiment illustrated, track roller assembly 120 includes two roller bearing assemblies 149 with one roller bearing assembly 149 on each side. Each roller bearing assembly 149 may be adjacent shaft flange 144.

In the embodiment illustrated in FIG. 3, track roller assembly 120 includes a sensor 150 that detects sensed feature 135 as roller 130 rotates about roller shaft 140. Sensor 150 may be used to detect track roller 130 revolutions and to determine, inter alia, the rotational speed of roller 130. Sensor 150 may be a magnetic speed sensor, an optical sensor, or any other type of sensor that may be used to detect sensed feature 135. Sensor 150 may be embedded into roller shaft 140. In the embodiment illustrated, sensor 150 is located in shaft flange 144 with both shaft flange 144 and sensor 150 being configured to axially align with sensed feature 135 relative to roller axis 123. Sensor 150 may be electronically connected to the electronic control system 200. In the embodiment illustrated, a wire 151 extends through roller shaft 140 and couples to sensor 150. Wire 151 may be directed along the track roller frame assembly 110 and up to the electronic control system 200.

Figure 4:
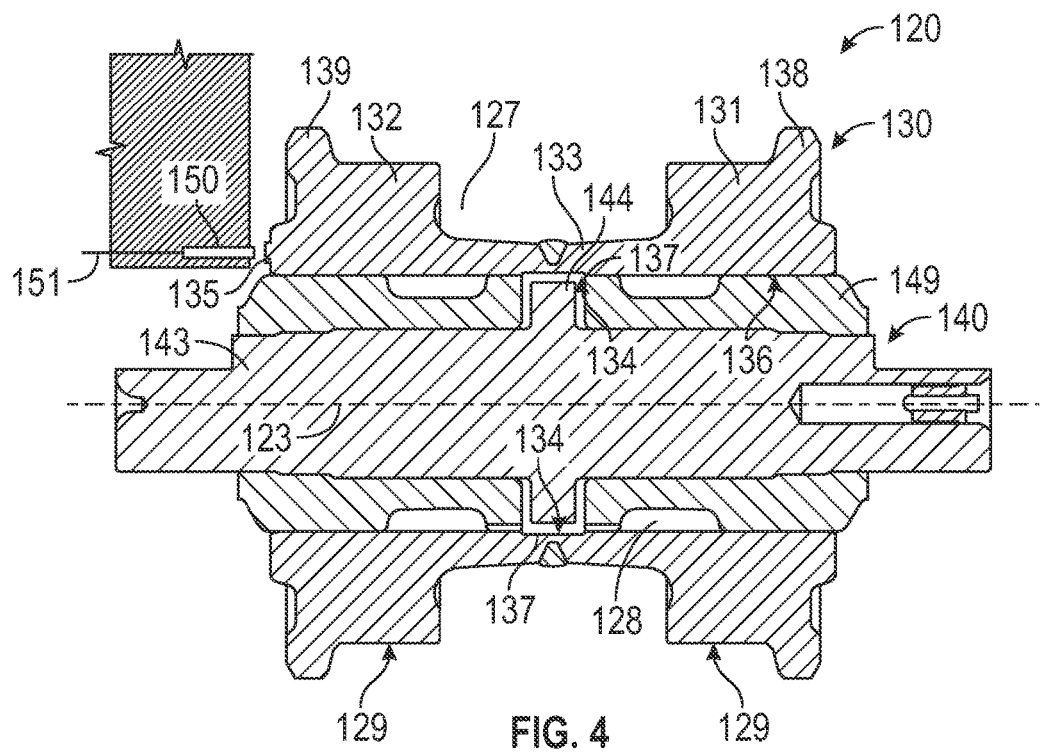
FIG. 4 is a cross-sectional view of an alternate embodiment of a track roller assembly of FIGS. 1 and 2.

FIG. 4 is a cross-sectional view of an alternate embodiment of a track roller assembly 120 of FIGS. 1 and 2. In the embodiment illustrated in FIG. 4, sensed feature 135 is located on and extends axially from a side 126 of roller 130. Side 126 may include the side of body 133 including the side of either first roller contact flange 131 or second roller contact flange 132. In other embodiments, sensed feature 135 extends axially into body 133 from side 126 and is a slot that is the inverse of the tooth illustrated in FIG. 4. Side 126 may generally be facing in the axial direction relative to roller axis 123. In the embodiment illustrated in FIG. 4, sensor 150 is mounted to or connected to supporting structure 66 and is axially adjacent sensed feature 135 without touching sensed feature 135 and is radially aligned with sensed feature 135.

Figure 5:
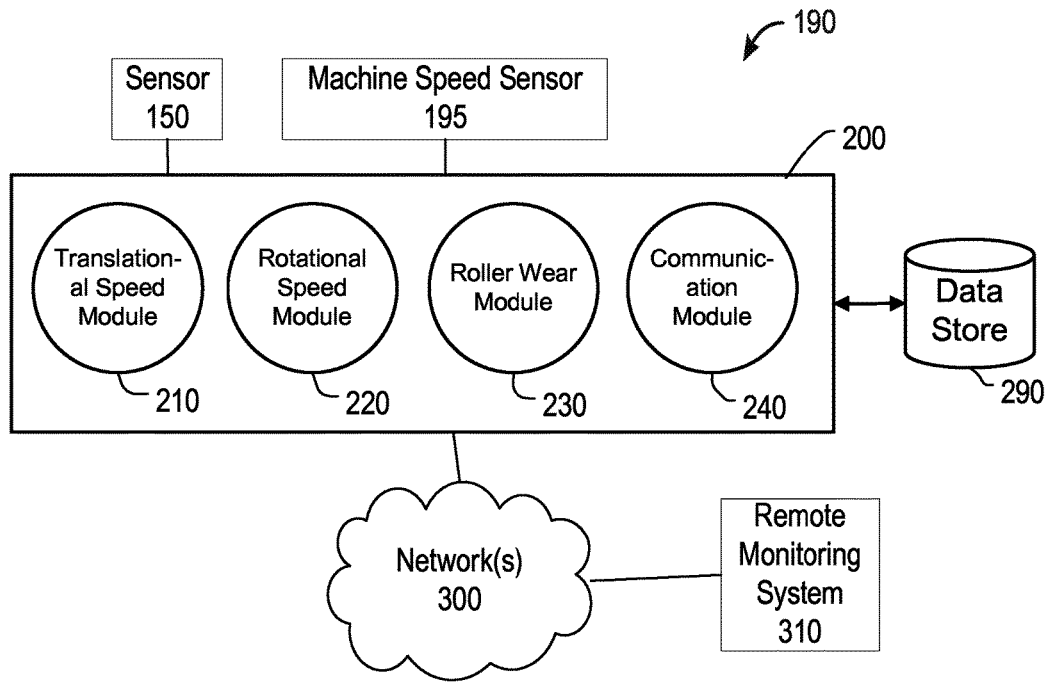
FIG. 5 is a functional block diagram of a Wear system for determining the wear for the rollers of FIGS. 4 and 5.

FIG. 5 is a functional block diagram of a Wear system 190 for determining the wear for the rollers 130 of FIGS. 4 and 5. Wear system 190 may include a machine speed sensor 195, the sensor 150, and the electronic control system 200. Machine speed sensor 195 is electronically connected to electronic control system 200 and is configured to measure one or more parameters related to the speed of the machine 50 and provide a translational input signal, such as the speed of the machine 50 or parameters related to the speed of the machine 50, to the electronic control system 200. Sensor 150 is configured to detect when sensed feature 135 rotates past sensor 150 and is configured to provide a rotational input signal, including when sensor 150 detects sensed feature 135, to the electronic control system 200.

Electronic control system 200 can be hardware, one or more software modules executed by a processor (e.g., of a computer), or a combination of the two. A software module can reside in processor readable memory. In embodiments, electronic control system 200 includes a machine speed module 210, a roller speed module 220, and a roller wear module 230. The machine speed module 210 is configured to obtain the speed of machine 50 using the translational input signal. The machine speed module 210 may obtain the speed of machine 50 by receiving the speed directly from machine speed sensor 195 or by determining the speed of machine 50 from the one or more parameters related to the speed of the machine 50 measured by machine speed sensor 195. The roller speed module 220 is configured to use the rotational input signal, such as a roller rotational count, to determine the rotation speed (angular velocity) of the roller 130.

Roller wear module 230 is configured to determine the wear on roller 130 at roller contact surface 129 based on the revolutions of the roller 130 detected by the sensor 150. Wear on roller 130 will cause the size parameters, such as the circumference, the radius, and the diameter, of roller contact surface 129 to reduce over time. As the size parameters reduce, the roller 130 will rotate faster to travel the machine to travel same distance. Roller wear module 230 uses the rotational speed relative to the machine speed to determine at least one of the size parameters of the roller contact surface 129. In some embodiments, machine speed module 210 provides an average machine speed over a predetermined amount of time and the roller speed module 220 provides an average rotational speed for the roller 130 over the predetermined amount of time. Similarly, roller wear module 230 may provide an average of at least one of the size parameters of the roller contact surface 129. The predetermined amount of time for averaging the speeds may be any time long enough to provide a statistically significant sample size of the speeds, such as one minute, one hour, one day, or an operation cycle of the machine 50.

In some embodiments, roller wear module 230 determines the wear using the rotational speed of roller 130 and the information provided by the translational speed signal, without directly determining the translational speed of the machine 50. In some embodiments, roller wear module 230 determines the wear, such as one of the size parameters of the roller contact surface 129, using the rotational speed signal without directly determining the rotational speed of roller 130.

The wear system 190 may include a data store 290. The translational speed data, the rotational speed data, and the wear data may be stored in the data store 290. This may include the histogram data of each. The data store 290 may be local to the electronic control system 200 or may be remotely located to the electronic control system 200.

Electronic control system 200 may also include a communication module 240. Communication module 240 may be configured to provide a signal to an operator when the wear on roller 130 reaches a threshold, such as a size parameter of the roller contact surface 129 reaching a predetermined value.

In some embodiments, wear system 190 includes a remote monitoring system 310 connected to the electronic control system 200 over a network 300. The remote monitoring system 310 may be maintained by the owner of the machine 50 or by the original equipment manufacturer of the machine 50. The communication module 240 may be configured to send the determined roller wear, such as one or more of the size parameters of the roller contact surface 129, to the remote monitoring system 310. In some embodiments, communication module 240 is configured to send the average rotational and translational speeds to the remote monitoring system 310 and the wear is determined by the remote monitoring system 310. The communication module 240 may be configured to send the data to the remote monitoring system 310 on a regular interval, such as a daily interval, weekly interval, monthly interval, or quarterly interval.

INDUSTRIAL APPLICABILITY

Machines, such as hydraulic mining shovels, excavators, wheel loaders, cable shovels, bucket wheels, bulldozers, and draglines are commonly used in the construction and mining industries to dig, excavate, move, and load materials, such as rock soil, overburden, and ore during mining and construction processes. In heavy duty applications, these machines can weigh 1,500 tons or more. The undercarriage track systems including the rollers and one or more track chain assemblies formed by interconnected track links or pads are often subject to high stresses and wear.

Wear on the rollers generally occurs over an extended period of time and may be difficult to predict. Providing a roller 130 with a sensed feature 135 allows the wear on the roller 130 to be determined at any given time during operation of the machine 50. The measured wear on the roller 130 may help an original equipment manufacturer or an owner of the machine monitor and track the wear on roller 130. The data related to the wear on the roller 130 may be used to predict when the roller 130 should be replaced and may help determine an optimal time to service the machine 50.

Figure 6:
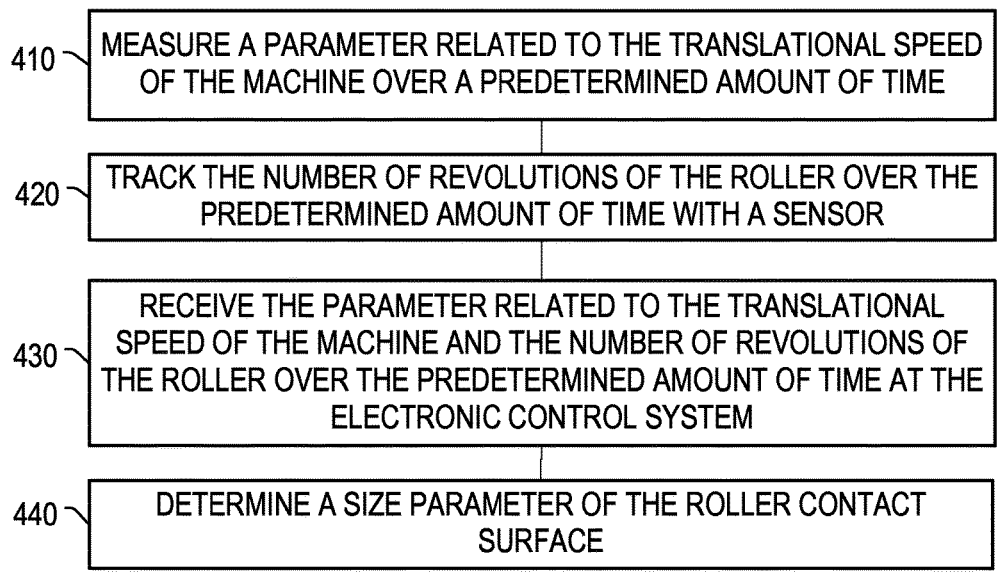
FIG. 6 is a flowchart of a method for determining the wear on a roller.

FIG. 6 is a flowchart of a method for determining the wear on a roller 130. The method includes measuring a parameter related to the translational speed of the machine 50 over a predetermined amount of time at step 410. The method also includes tracking the number of revolutions of the roller 130 over the predetermined amount of time with a sensor 150 at step 420. The method further includes receiving the parameter related to the translational speed of the machine 50 and the number of revolutions of the roller 130 over the predetermined amount of time at the electronic control system 200 at step 430. The method yet further includes determining a size parameter of the roller contact surface 129 at step 440. Step 440 may include determining a rotational speed of the roller 130 and obtaining a translational speed of the machine 50. In some embodiments, step 440 includes determining an average rotational speed of the roller 130 and an average translational speed of the machine 50. In some embodiments, the method includes sending the determined size parameter from the electronic control system 200 to a remote monitoring system 310 for analysis. In other embodiments, the method includes sending the parameter related to the translational speed of the machine 50 and the number of revolutions of the roller 130 over the predetermined amount of time from the electronic control system 200 to the remote monitoring system 310 and determining the size parameter of the roller contact surface 129 at the remote monitoring system 310.

Those of skill will appreciate that the various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the design constraints imposed on the overall system. Skilled persons can implement the described functionality in varying ways for each particular application, but such implementation decisions should not be interpreted as causing a departure from the scope of the invention. In addition, the grouping of functions within a module, block, or step is for ease of description. Specific functions or steps can be moved from one module or block without departing from the invention.

The various illustrative logical blocks and modules described in connection with the embodiments disclosed herein can be implemented or performed with a general purpose processor, a digital signal processor (DSP), application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor (e.g., of a computer), or in a combination of the two. A software module can reside, for example, in RAM memory, flash memory, ROM memory, EPROM memory, EEPROM memory, registers, hard disk, a removable disk, a CD-ROM, or any other form of storage medium. An exemplary storage medium can be coupled to the processor such that the processor can read information from, and write information to, the storage medium. In the alternative, the storage medium can be integral to the processor. The processor and the storage medium can reside in an ASIC.

The preceding detailed description is merely exemplary in nature and is not intended to limit the invention or the application and uses of the invention. The described embodiments are not limited to use in conjunction with a particular type of machine. Hence, although the present disclosure, for convenience of explanation, depicts and describes particular machine, it will be appreciated that the track roller assembly and electronic control system in accordance with this disclosure can be implemented in various other configurations and can be used in other types of machines. Furthermore, there is no intention to be bound by any theory presented in the preceding background or detailed description. It is also understood that the illustrations may include exaggerated dimensions to better illustrate the referenced items shown, and are not consider limiting unless expressly stated as such.

What is claimed is:

1. A track roller assembly of an undercarriage track system for a machine, the track roller assembly comprising:
   a roller including
      a body formed as a solid of revolution about a roller axis, the body including
         a bore surface defining a bore extending through the body, the bore surface being a radially inner surface of the body and being a cylindrical shape, and
         a roller contact surface located outward from the bore surface, the roller contact surface being a surface of revolution about the roller axis, and
      a sensed feature protruding from the body into the bore;
   a roller shaft including a shaft body extending through the bore;
   a bearing disposed between the roller and the shaft; and
   a sensor embedded in the shaft body, the sensor being axially aligned with the sensed feature and radially positioned to detect the sensed feature when the sensed feature rotates past the sensor.

2. The track roller assembly of claim 1, wherein the shaft body includes a shaft flange axially aligned with the sensed feature and the sensor is embedded in the shaft flange.

3. The track roller assembly of claim 1, wherein the sensor is a magnetic speed sensor.

4. The track roller assembly of claim 1, wherein the sensed feature is a tooth extending from and integral to the body.

5. The track roller assembly of claim 1, wherein the body includes a first roller contact flange and the roller contact surface is an outer surface of the first roller contact flange.

6. The track roller assembly of claim 5, wherein the body includes a second roller contact flange spaced apart from the first roller contact flange forming an outer recess there between, the second roller contact flange including a second roller contact surface.

7. The track roller assembly of claim 1, further comprising a wire extending from the sensor and through the shaft.

8. A wear system including the track roller assembly of claim 1, the wear system further comprising an electronic control system electronically connected to the sensor, the electronic control system being configured to determine a size parameter of the roller based on revolutions of the roller detected by the sensor, the size parameter being related to wear of the roller.

* * * * *